United States Patent [19]  
Green et al.

[11] 4,091,113  
[45] * May 23, 1978

[54] RANDOMLY TERMINATED CAPPED POLYMERS

[75] Inventors: Harold A. Green, Havertown, Pa.; John J. Merianos, Jersey City; Alfonso N. Petrocci, Glen Rock, both of N.J.

[73] Assignee: Kewanee Industries, Inc., Bryn Mawr, Pa.

[*] Notice: The portion of the term of this patent subsequent to May 31, 1994, has been disclaimed.

[21] Appl. No.: 789,447

[22] Filed: Apr. 20, 1977

Related U.S. Application Data

[63] Continuation-in-part of Ser. No. 610,168, Sep. 4, 1975, Pat. No. 4,027,020, which is a continuation-in-part of Ser. No. 518,596, Oct. 29, 1974, Pat. No. 3,931,319.

[51] Int. Cl.$^2$ .................. A01N 9/20; A01N 9/24; C07C 87/28; C07C 87/10
[52] U.S. Cl. .................. 424/329; 260/567.6 P; 424/244; 424/248.56; 424/248.57; 424/249; 424/258; 424/267
[58] Field of Search .............. 424/329, 248.56, 248.57, 424/267, 244, 258, 249; 260/567.6 P

[56] References Cited

U.S. PATENT DOCUMENTS

| | | | |
|---|---|---|---|
| 1,797,877 | 3/1931 | Moore | 260/567.6 P |
| 2,261,002 | 10/1941 | Ritter | 260/567.6 P |
| 2,375,853 | 5/1945 | Kirby et al. | 260/567.6 P |
| 2,388,614 | 11/1945 | Kirby et al. | 260/567.6 P |
| 2,525,777 | 10/1950 | de Benneville | 260/567.6 P |
| 2,817,664 | 12/1957 | Cavallito et al. | 260/567.6 P |
| 2,933,529 | 4/1960 | Hwa | 260/567.6 P |
| 3,079,436 | 2/1963 | Hwa | 260/567.6 P |
| 3,825,511 | 7/1974 | Markhart et al. | 526/259 |

FOREIGN PATENT DOCUMENTS

| | | | |
|---|---|---|---|
| 536,017 | 4/1941 | United Kingdom | 260/567.6 P |
| 750,346 | 6/1956 | United Kingdom | 260/567.6 P |

*Primary Examiner*—Albert T. Meyers  
*Assistant Examiner*—D. W. Robinson  
*Attorney, Agent, or Firm*—Arthur A. Jacobs

[57] ABSTRACT

Anti-microbial polymeric quaternary ammonium compounds and mixtures thereof, having linear chains which terminate in quaternary ammonium moieties, such compounds being formed by polymerization which is carried out in such a manner that the linear chains thereof are terminated in random fashion, the reaction resulting in the formation of the compounds being a one-step reaction between 1,4-dihalo-2-butene and a mixture of a difunctional tertiary amine and a monofunctional tertiary amine wherein the molar quantity of the difunctional amine is greater than the molar quantity of the monofunctional amine. These products are especially effective hair conditioning agents.

6 Claims, No Drawings

RANDOMLY TERMINATED CAPPED POLYMERS

This application is a continuation-in-part of application Ser. No. 610,168, filed Sept. 4, 1975, now U.S. Pat. No. 4,027,020 which in turn, is a continuation-in-part of application Ser. No. 518,596, filed Oct. 29, 1974, now U.S. Pat. No. 3,931,319.

This invention relates to quaternary ammonium polymers and mixtures thereof, in which the ammonium moieties are part of the linear polymeric chains, and not branches appended to the linear chain. Even more particularly, they are quaternary ammonium polymers in which the linear chains terminate in quaternary ammonium moieties, thereby making further chain propagation impossible under the conditions of the experimental procedures by which the polymers are synthesized. Furthermore, polymerization is carried out in such a manner that the chain lengths, and therefore the molecular weights, of the polymers vary over a wide range because polymerization is halted and the chains are terminated in random fashion. Accordingly, the products of this invention are called "randomly terminated" quaternary ammonium polymers.

The products of this invention may be synthesized by causing 1,4-dihalo-2-butene to react in a one-step reaction with a mixture of a difunctional tertiary amine and a monofunctional tertiary amine. The molar quantity of the difunctional amine must be considerably greater than the molar quantity of the monofunctional amine in the mixture, the molar ratios of diamine to monoamine being from about 2 to 1, to about 30 to 1.

In the starting materials the number of terminal halogen moieties in the 1,4-dihalo-2-butene should be approximately equal to the total number of tertiary amino groups. Since the diamine and the dihalo compounds each have two reactive equivalents, but the monoamine has only one reactive equivalent, the proper ratios of starting materials can be achieved when the number of moles of 1,4-dihalo-2-butene is approximately equal to the sum of the number of moles of diamine and one-half the number of moles of monoamine.

The difunctional tertiary amine may be represented by the structural formula:

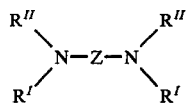

For purposes of clarification, Z represents either (1) a divalent aliphatic radical of from 2 to 10 carbon atoms containing from 0 to 2 hydroxyl substituents and from 0 to 2 ethylenic double bonds, and $R^I$ and $R^{II}$ may either be (A) the same or different and may be either (a) an alkyl group of from 1 to 20 carbon atoms having from 0 to 2 hydroxyl substituents, (b) benzyl, (c) benzyl in which the benzene moiety has one alkyl substituent of from 2 to 20 carbon atoms, and (d) benzyl in which the benzene moiety has from 1 to 5 methyl substituents; (B) $R^I$ and $R^{II}$, taken together with N, form a saturated or unsaturated heterocyclic ring of from 5 to 7 atoms; or (C) $R^I$ and $R^{II}$, taken together with N, may be combined with an oxygen atom to form a N-morpholino group; or (2) Z represents two divalent ethylene radicals, in which case $R^{II}$ is absent and $R^I$ represents (a) an aliphatic radical of from 1 to 20 carbon atoms having from 0 to 2 hydroxyl substituents, (b) benzyl, (c) benzyl in which the benzene moiety has an alkyl substituent of from 2 to 20 carbon atoms, or (d) benzyl in which the benzene moiety has from 1 to 5 methyl substituents; or (3) Z represents three divalent ethylene radicals in which case $R^I$ and $R^{II}$ are both absent.

The monotertiary amine may be represented by the structural formula:

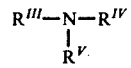

where (1) $R^{III}$ is an aliphatic radical of from 1 to 20 carbon atoms, having from 0 to 2 hydroxyl substituents, and $R^{IV}$ and $R^V$ may be either (a) the same or different and represent an aliphatic radical having from 1 to 4 carbon atoms with from 0 to 1 hydroxyl substituents; (b) taken together with N to form a saturated or unsaturated heterocyclic ring of from 5 to 7 atoms; (c) taken together with N, and combined with an oxygen atom, to form a N-morpholino group; or where (2) $R^{III}$, $R^{IV}$, $R^V$ and N, taken together, may represent quinoline, isoquinoline or hexamethylene tetramine.

A method has been proposed wherein the polymeric quaternary compound are made by a two-step synthesis. In the first step 1,4-dihalo-2-butene was reacted with slightly less than a molar quantity of a ditertiary amine. Under the conditions of this reaction, polymerization proceeds until the diamine is depleted. Because of the initial excess of dihalo butene over diamine in the reaction mixture, the polymeric chains have termini of halogen atoms, thereby making the ends of the chain reactive toward the addition of more amine. After the unreacted dichlorobutene is removed by extraction at the completion of the first step, a calculated quantity of monotertiary amine is added to the polymeric residue for the second step of the synthesis.

The chemical quaternization which ensues from the above reaction results in the formation of polymers with quaternary ammonium termini. Since these quaternized ends of the chain are incapable of further chain propagation reactions with dihalobutene, the polymer is said to be "capped" in the second step.

The second step merely "caps" the polymeric products of the first step. Therefore, the chain lengths and molecular weights of the products are determined in the first step. Since the polymerization of the first step proceeds in a sustained fashion until all of the diamine is exhausted, the chain lengths are comparatively long because the number of condensations is comparatively high. Furthermore, since the propagation of chains is permitted to proceed uninterruptedly under conditions where each chain has equal probability to participate in the propagation reaction, the product of the first step, and subsequently the product of the second step, is a mixture of polymeric products whose chain lengths and molecular weights fall within a comparatively narrow range.

In accordance with the present invention, on the other hand, the products are made by a single-step synthesis in which both ditertiary amine and monotertiary amine are mixed simultaneously with the 1,4-dihalo-2-butene, there being about a 1:1 ratio of halogen equivalents to the total number of tertiary amine equivalents. The molar ratio of diamine to monoamine in the initial reaction mixture is about 2:1 to about 30:1. The reaction takes place at reflux temperature, which is usually between about 50°–70° C, while the reaction time may vary depending on the reactants as well as the temperature, but is usually about 1 to 10 hours.

In both the two-step and the one-step process, the terminal halogen atoms of a chain may participate in chain propagation reactions by being displaced by one of the amine groups of a diamine, thereby making a quaternary nitrogen. Chain propagation is possible because the second amine of the diamine is capable of reacting with a dihalo molecule. However, in the one-step process there is also an alternative route. The terminal halogen of a chain may react with a monoamine, instead of a diamine. The reaction with a monoamine gives rise to quaternary ammonium terminus which is incapable of further chain propagation by reaction with a dihalo molecule. In this manner, any chain may become "capped" while other chains are propagating. Therefore, the product of the present invention, in which both diamine and monoamine are used in the initial reaction mixture, is the resultant of two competing reactions, one a propagation reaction when the diamine reacts with the terminal halogen and the other a "capping" reaction, when the monoamine reacts.

The products made by the two different processes are unlike both in their chemical and physical properties. In this respect, because of the presence of monoamine during chain propagation, there is always a possibility that a chain termination reaction will occur and terminate chain propagation abruptly. Therefore, every chain cannot grow uninterruptedly. Some chains will continue to grow while others will terminate, depending on whether the terminal halogen reacts with a diamine or monoamine.

Furthermore, some chains are terminated quite early, leaving only small chains, whereas other chains are terminated only after having undergone a large number of propagation reactions. Termination occurs in a statistically random fashion. Therefore, the chain lengths vary from very short to very long, and the molecular weights vary from low to high, over a comparatively wide range.

This is in contrast to the prior products in which the polymeric quaternary compounds were all of comparatively high molecular weights, and varied over a comparatively narrow range.

The compounds of this invention, or mixtures of these compounds, have been discovered to be uniquely excellent hair conditioning agents, and are also compatible in binary or tertiary systems with most of the lathering and cleansing surfactants used in hair conditioning consumer products.

Although many hair conditioning agents are on the market, they are generally subject to one or more disadvantages. For example, they may not be adequately water-soluble, or they may not be sufficiently non-toxic or non-irritating, or they may not be sufficiently substantive to the hair, or they may not be sufficiently compatible with detergents of the type that are usually used in washing the hair.

In accordance with the present invention, all of the aforesaid disadvantages are overcome by using as a hair conditioner the water soluble linear polyquaternary ammonium products of the present invention.

The present products are substantially non-toxic. In this respect, 40% aqueous solutions have been found to have an "LD-50" of between 4.21 ml. and 4.71 ml. per kilogram of body weight, as determined in accordance with the method of Litchfield, and Wilcoxon, described in the "Journal of Pharmacology and Experimental Therepeutics", Vol. 96 pg. 99, 1949. Based on density of 1.15 for the 40% aqueous solutions, the "LD-50" is 1.9 grams to 2.2 grams of pure active material per kilogram of body weight. These results show a sufficient lack of toxicity for the purposes of the present invention.

40% aqueous solutions are also non-irritating to the skin and are not primary irritants. These evaluations were made in accordance with the method of Draize, as described in "Appraisal of the Safety of Chemicals in Food, Drugs, and Cosmetics", published by the Association of Food and Drug Officials of the United States.

The products of the present invention are also non-irritating to the eyes when applied directly to the eyes in concentrations of 4% in accordance with the method of Draize as described in the aforesaid "Approval of the Safety of Chemicals in Foods, Drugs, and Cosmetics."

The products' efficiency as a hair conditioner is shown by the fact that in concentrations as low as $\frac{1}{2}$ of 1% they impart a smooth feeling to hair, and in concentrations as low as 1%, they promote easy detangling of hair, and facilitate hair combing by eliminating or diminishing "drag".

When properly formulated into cream rinses or shampoos, the products are highly substantive to hair; but, more importantly, even with successive rinsing and shampooing, there is no noticable buildup of insoluble solid matter on the hair, as is the case with most hair-conditioning agents, especially those which comprise water-insoluble, high molecular weight polymers.

A maximum adsorption of the products of this invention on the hair is reached almost immediately, after which no further deposit occurs. Consequently, there is no unsightly flaking or deposited conditioning agent with continued use.

The present products are compatible with cationic surfactants and emulsifiers, such as quaternary ammonium salts; with non-ionic surfactants and emulsifiers, such as alkyl or aryl polyethyleneoxy alcohols; with amine oxide surfactants and emulsifiers; with alkylolamide surfactants; with amphoteric surfactants and emulsifiers such as "Miranols", and derivatives of aminoacetic acid and $\beta$-aminopropionic acid, and the like; and with surfactant and emulsifier betaines and betaine salts. It is also compatible with the common non-ionic cosmetic thickeners such as methyl cellulose, ethyl cellulose, hydroxyethyl cellulose and hydroxypropyl cellulose.

Despite the fact that they are cationic, the present product are quite surprisingly, compatible with certain anionic surfactants and emulsifiers such as salts of N-alkyl glycinates, N-alkyl sarcosinates N-alkyl $\beta$-aminopropionates, and alkyl or aryl polyethyeneoxy sulfates. But, even more surprisingly, they can be made compatible with such anionic surfactants as alkyl sulfates and alkylaryl sulfonates, and the like, when these anionics are used in combination with amphoteric or betaine type surfactants and emulsifiers in ternary systems.

Therefore, the products of this invention may be used as components not only of clear or opacified hair rinse, but of clear or opacified shampoos that can contain high-latering surfactants.

The present products also have the property that, whether used as an additive in shampoos or in hair rinses, they impart a certain amount of "body" to the hair because of their substantive properties. Furthermore, when used as an additive in shampoos, they endow the wet hair with "cream rinse" properties because the wet hair is easily detangled and combed out.

When they are used in a "setting lotion" or a "cream rinse", they allow the hair to hold a tight curl or "set" with greater efficiency and for longer periods of time then the ordinary hair-conditioners that were tested. The products of this invention retain their hair conditioning properties in aqueous solution as well as in oil-in-water emulsions.

In addition to their hair conditioning properties in aqueous solution or in oil-in-water emulsions, the present products function as good emulsifiers for water-in-oil emulsions. In this respect, they have been used as the sole emulsifier in water-in-oil emulsions with an oil content as high as 80%.

Although all of the compounds of the present invention displayed good hair conditioning properties, the product of Example 4 is herein used as representative of such compounds generally.

The following examples are illustrative of the present invention:

EXAMPLE 1

522 grams of morpholine (6 moles) were cooled at 20° C and 125 grams of 1,4-dichloro-2-butene (1 mole) were added dropwise with constant stirring and cooling to keep the temperature at 50°–60° C. The entire addition took about 1 hour, and stirring was continued for about one more hour. While stirring, 150 grams of water were poured into the reaction mixture, followed by 200 grams of 50% sodium hydroxide solution; then the mixture was allowed to separate.

The organic layer was removed, and the unreacted morpholine was removed by distillation under reduced pressure. The residue was washed with water and filtered, yielding a yellow solid melting at 79°–83° C. This was 1,4-bis-(N-morpholino)-2-butene.

Since the purpose of the excess morpholine was to act as an acid acceptor, the experiment was repeated, but with 212 grams of sodium carbonate (2 moles) replacing the excess 174 grams of morpholine (4 moles). The yield of 1,4-bis-(N-morpholino)-2-butene was about the same as the previous synthesis.

This reaction was repeated using 0.1 mole of 1,4-dichloro-2-butene and 0.6 mole of the following amines in place of morpholine: piperidine, homopiperidine, diethanolamine, dimethylamine, dipropylamine, dibutylamine, di-(2-ethylhexyl) amine, dioctylamine, didecylamine, didodecylamine, N-methyl propylamine, N-methyl butylamine, N-methyl hexylamine, N-methyl octylamine, N-methyl decylamine, N-methyl dodecylamine. All of these 1,4-bis-amino-2-butenes were liquids, and were recovered from their aqueous mixtures by partitioning.

EXAMPLE 2

28.4 grams of 1,4-bis-dimethylamino-2-butene (0.2 moles) and 1.49 grams of triethanolamine (0.01 moles) were dissolved in about 55.5 grams of water in a round-bottom flask fitted with a stirrer and reflux condenser, and 25.63 grams of 1,4-dichloro-2-butene (0.205 moles) were added slowly while the mixture was stirred. The reaction mixture was heated at 60°–70° C and maintained at that temperature, with stirring, for about 6 hours. The reaction was 98% complete, as indicated by ionic chloride analysis. The residue contained about 50%, by weight, of active material.

The procedure of Example 2 was repeated several times using different proportions of reactants, as follows:

|  | Example 3 | Example 4 | Example 5 | Example 6 | Example 7 |
|---|---|---|---|---|---|
| 1,4-bis-dimethylamino-2-butene | 28.4 grams (0.2 moles) | 28.4 grams (0.2 moles) | 28.4 grams (0.2 moles) | 28.4 grams (0.2 moles) | 28.4 grams (0.2 moles) |
| triethanol amine | 2.98 grams (0.02 moles) | 5.96 grams (0.04 moles) | 8.94 grams (0.06 moles) | 11.92 grams (0.08 moles) | 14.9 grams (0.1 moles) |
| 1,4-dichloro-2-butene | 26.25 grams (0.21 moles) | 27.5 grams (0.22 moles) | 28.3 grams (0.23 moles) | 30.0 grams (0.24 moles) | 31.3 grams (0.25 moles) |
| Water | 57.7 grams | 61.9 grams | 65.7 grams | 70.3 grams | 74.6 grams |

The procedure of Example 2 was again repeated, except that the following reactants were used:

EXAMPLE 8

28.4 grams of 1,4-bis-dimethylamino-2-butene (0.2 moles)
1.94 grams of N-methyl morpholine (0.02 moles)
26.25 grams of 1,4-dichloro-2-butene (0.21 moles)
56.6 grams of water

EXAMPLE 9

28.4 grams of 1,4-bis-dimethylamino-2-butene (0.2 moles)
2.00 grams of N-methyl piperidine (0.02 moles)
26.25 grams of 1,4-dichloro-2-butene (0.21 moles)
56.7 grams of water

EXAMPLE 10

28.4 grams of 1,4-bis-dimethylamino-2-butene (0.2 moles)
2.06 grams of N-methyl homopiperidine (0.02 moles)
26.5 grams of 1,4-dichloro-2-butene (0.21 moles)
56.7 grams of water

EXAMPLE 11

28.4 grams of 1,4-bis-dimethylamino-2-butene (0.2 moles)
1.7 grams of N-methyl pyrrolidine (0.02 moles)
26.5 grams of 1,4-dichloro-2-butene (0.21 moles)
56.6 grams of water

EXAMPLE 12

28.4 grams of 1,4-bis-dimethylamino-2-butene (0.2 moles)
2.02 grams of butyldimethylamine (0.02 moles)
26.5 grams of 1,4-dichloro-2-butene (0.21 moles)
56.9 grams of water

EXAMPLE 13

28.4 grams of 1,4-bis-dimethylamino-2-butene (0.2 moles)
2.3 grams of pentyldimethylamine (0.02 moles)
26.5 grams of 1,4-dichloro-2-butene (0.21 moles)
57.2 grams of water

EXAMPLE 14

28.4 grams of 1,4-bis-dimethylamino-2-butene (0.2 moles)
2.58 grams of hexyldimethylamine (0.02 moles)

26.5 grams of 1,4-dichloro-2-butene (0.21 moles)
57.5 grams of water

EXAMPLE 15

28.4 grams of 1,4-bis-dimethylamino-2-butene (0.2 moles)
2.86 grams of heptyldimethylamine (0.02 moles)
26.5 grams of 1,4-dichloro-2-butene (0.21 moles)
57.8 grams of water

EXAMPLE 16

28.4 grams of 1,4-bis-dimethylamino-2-butene (0.2 moles)
3.14 grams of octyldimethylamine (0.02 moles)
26.5 grams of 1,4-dichloro-2-butene (0.21 moles)
58.1 grams of water

EXAMPLE 17

28.4 grams of 1,4-bis-dimethylamino-2-butene (0.2 moles)
3.42 grams of nonyldimethylamine (0.02 moles)
26.5 grams of 1,4-dichloro-2-butene (0.21 moles)
58.3 grams of water

EXAMPLE 18

28.4 grams of 1,4-bis-dimethylamino-2-butene (0.2 moles)
3.7 grams of decyldimethylamine (0.02 moles)
26.5 grams of 1,4-dichloro-2-butene (0.21 moles)
58.6 grams of water

EXAMPLE 19

28.4 grams of 1,4-bis-dimethylamino-2-butene (0.2 moles)
3.98 grams of undecyldimethylamine (0.02 moles)
26.5 grams of 1,4-dichloro-2-butene (0.21 moles)
58.9 grams of water

EXAMPLE 20

28.4 grams of 1,4-bis-dimethylamino-2-butene (0.2 moles)
4.26 grams of dodecyldimethylamine (0.02 moles)
26.5 grams of 1,4-dichloro-2-butene (0.21 moles)
59.2 grams of water

EXAMPLE 21

28.4 grams of 1,4-bis-dimethylamino-2-butene (0.2 moles)
2.7 grams of benzyldimethylamine (0.02 moles)
26.5 grams of 1,4-dichloro-2-butene (0.21 moles)
57.6 grams of water

EXAMPLE 22

28.4 grams of 1,4-bis-dimethylamino-2-butene (0.2 moles)
2.62 grams of quinoline (0.02 moles)
26.5 grams of 1,4-dichloro-2-butene (0.21 moles)
57.5 grams of water

EXAMPLE 23

28.4 grams of 1,4-bis-dimethylamino-2-butene (0.2 moles)
2.62 grams of isoquinoline (0.02 moles)
26.5 grams of 1,4-dichloro-2-butene (0.21 moles)
57.5 grams of water

EXAMPLE 24

28.4 grams of 1,4-bis-dimethylamino-2-butene (0.2 moles)
2.8 grams of hexamethylenetetramine (0.02 moles)
26.5 grams of 1,4-dichloro-2-butene (0.21 moles)
57.7 grams of water Although in Examples 2 to 24 above, the difunctional tertiary amine 1,4-bis-dimethylamino-2-butene was utilized, any of the other difunctional tertiary amines, as disclosed in Example 1, may be substituted in equivalent molar amounts. Illustrative of such other difunctional amines are, for example, 1,4-bis-(N-morpholino)-2-butene; 1,4-N,N'-dimethylpiperazine; 1,4-diazabicyclo (2.2.2) octane; N,N,N',N'-tetramethylethylene diamine; N,N,N',N'-tetra-(2-hydroxylpropyl)ethylene diamine; 1,3-bis-(dimethylamino)-2-hydroxypropane; and 1,4-di-(N-homopiperidino)-2-butene.

Furthermore, although only 1,4-dichloro-2-butene has been illustrated above, 1,4-dibromo or 1,4-diiodo-2-butene may be substituted.

EXAMPLE 25

28.4 grams of 1,4-bis-dimethylamino-2-butene (0.2 moles)
1.01 grams of butyldimethylamine (0.01 moles)
25.63 grams of 1,4-dichloro-2-butene (0.205 moles)
55.04 grams of water

EXAMPLE 26

28.4 grams of 1,4-bis-dimethylamino-2-butene (0.2 moles)
0.97 grams of N-methyl morpholine (0.01 moles)
25.63 grams of 1,4-dichloro-2-butene (0.205 moles)
55.0 grams of water

EXAMPLE 27

The "Broth Dilution Test" method was used to assay the antimicrobial properties of the products. In this method, 1.0 ml. of a solution of the material being tested was added to 9.0 ml. of a suitable broth culture medium in a test tube. A series of such test tubes was prepared so that there was presented a stepwise decrease in the concentrations being tested, from 0.1% (1000 ppm) to 0.005% (50 ppm). Each tube was then inoculated with 0.1 ml. of either a 24-hour broth culture of test bacteria, or a 14-day aqueous spore suspension of test fungi. The testing program was designed so that every concentration of every material was inoculated separately with each organism used in the test.

The test organisms employed were:
*Escherchia coli* (E.c.)
*Pseudomonas aeruginosa* (Ps.a.)
*Staphylococcus aureus* (S.a.)
*Streptococcus faecalis* (S.f.)
*Aspergillus niger* (A.n.)
*Penicilium expansum* (P.e.)

After inoculation, the tubes were incubated as follows:
72 hours at 37° C for bacteria
14 days at 28° C for fungi Following incubation, the tubes were examined for the presence or absence of macroscopic growth as evidenced by the presence or absence turbidity.

The lowest concentration of the material being tested at which macroscopic growth was not evident was designated as the "Minimum Inhibitory Level" (M.I.L.)

Table 1, following, shows the M.I.L. of the products that were tested. The inhibitory concentrations are shown in parts per million:

Table 1

| Product Synthesized in Example No. | Gram Positive | | Gram Negative | | Fungi | |
|---|---|---|---|---|---|---|
| | E.c. | Ps.a. | S.a. | S.f. | A.n. | P.e. |
| 1 | 1000 | 1000 | 1000 | 1000 | >1000 | >1000 |
| 2 | 50 | 50 | 50 | 50 | >1000 | >1000 |
| 7 | 50 | 50 | 50 | 50 | >1000 | >1000 |
| 24 | 1000 | 1000 | 1000 | 1000 | >1000 | >1000 |
| 11 | 50 | 50 | 50 | 50 | >1000 | >1000 |
| 23 | 100 | 500 | 100 | 100 | >1000 | >1000 |
| 15 | 1000 | 1000 | 1000 | 1000 | >1000 | >1000 |
| 17 | 1000 | 1000 | 1000 | 1000 | >1000 | >1000 |

The results of these test show that every compound tested has anti-bacterial properties in concentrations as low as 0.1%, and even lower in many cases.

EXAMPLE 27

In order to estimate the bactericidal power of these compounds, the product prepared in Example 3 was assayed using the "Water Treatment Test".

The product was dissolved in sterile distilled water and diluted to the test concentration. Then 50 ml. of test solution was added aseptically to previously sterilized cotton-stoppered 125 ml. Erlenmeyer flasks. One set of flasks containing the product at concentrations of 25 ppm., 50 ppm., 100 ppm., 150 ppm., 200 ppm., 250 ppm., and 300 ppm., was inoculated by introducing into each flask 0.5 ml. of a 1/10 nutrient broth dilution of a 24-hour nutrient broth culture of Aerobacter aerogenes. Another set of flasks containing the product at the same concentrations was inoculated by introducing into each flask 0.5 ml of a 1/10 nutrient broth dilution of a 24-hour nutrient broth culture of Pseudomonas aeruginosa.

At intervals of 30, 60 and 180 minutes following inoculation a 1.0 ml. aliquot was withdrawn from each flask and added to 9.0 ml. of sterile azolectin/"Tween 80" neutralizer from which additional tenfold serial dilutions were prepared in sterile neutralizer solution.

Nutrient agar plates were prepared from $1 \times 10^{-2}$ and $1 \times 10^{-3}$ dilutions.

Simultaneously with each set of flasks, a control of sterile distilled water was similarly inoculated and aliquots were taken at the same time intervals at $1 \times 10^{-4}$, $1 \times 10^{-5}$, and $1 \times 10^{-6}$ dilutions.

For additional control purposes, and also for comparison purposes, simultaneous assays were performed with each set of flasks on "BTC 776", a powerful bactericidal agent used in water treatment, the chemical name of which is alkyl benzyl dimethyl ammonium chloride. It is manufactured and sold by Onyx Chemical Co. of Jersey City, N.J.

Table 2 shows the number of survivors of Aerobacter aerogenes and Table 3 shows the number of survivors of Pseudomonas aeruginosa ATCC $15442, following exposure at different concentrations for the indicated period of time. The numbers in the table must be multiplied by $1 \times 10^2$. Concentrations of the materials being tested are given in parts by million.

Table 2

| | Aerobacter Aerogenes | | | |
|---|---|---|---|---|
| Compound (Example No.) | Concentration (ppm) | No. of Surviving Bacteria per ml. ($\times 10^2$) After | | |
| | | 30 Min. | 60 Min. | 180 Min. |
| 3 | 5 | 78 | 43 | 3 |
| | 5 | 89 | 45 | 1 |
| | 5 | 39 | 19 | 0 |

Table 2-continued

| | Aerobacter Aerogenes | | | |
|---|---|---|---|---|
| Compound (Example No.) | Concentration (ppm) | No. of Surviving Bacteria per ml. ($\times 10^2$) After | | |
| | | 30 Min. | 60 Min. | 180 Min. |
| | 5 | 59 | 15 | 0 |
| | 5 | 47 | 12 | 0 |
| | 5 | 37 | 14 | 0 |
| | 5 | 57 | 7 | 0 |
| | 10 | 23 | 1.5 | 0 |
| | 10 | 27 | 3 | 0 |
| | 10 | 22 | 4 | 0 |
| | 10 | 20 | 2 | 0 |
| | 10 | 21 | 3 | 0 |
| | 10 | 21 | 3 | 0 |
| | 10 | 16 | 3 | 0 |
| | 15 | 0 | 0 | 0 |
| | 25 | 0 | 0 | 0 |
| | 25 | 0 | 0 | 0 |
| BTC (Control) | 0 | 20,900 | 26,500 | 28,700 |
| | 10 | 49 | 10 | 0 |
| | 10 | 37 | 8 | 0 |
| | 10 | 32 | 10 | 0 |
| | 10 | 43 | 14 | 0 |
| | 20 | 1 | 0 | 0 |
| | 20 | 2 | 0 | 0 |
| | 20 | 6 | 0 | 0 |
| | 20 | 4 | 0 | 0 |

Table 3

| | Pseudomonas Aeruginosa | | | |
|---|---|---|---|---|
| Compound (Example No.) | Concentration (ppm) | No. of Surviving Bacteria per ml. ($\times 10^2$) After | | |
| | | 30 Min. | 60 Min. | 180 Min. |
| 3 | 20 | 9 | 0 | 0 |
| | 20 | 15 | 1 | 0 |
| | 20 | 13 | 0 | 0 |
| | 25 | 1 | 0 | 0 |
| | 25 | 0 | 0 | 0 |
| | 0 | 92,500 | 91,500 | 91,000 |
| BTC (Control) | 10 | 1,260 | 180 | 0 |
| | 10 | 1,380 | 123 | 0 |
| | 10 | 1,460 | 118 | 0 |
| | 10 | 1,500 | 192 | 0 |
| | 15 | 214 | 16 | 0 |
| | 15 | 235 | 18 | 0 |
| | 20 | 208 | 57 | 0 |
| | 20 | 137 | 15 | 0 |
| | 20 | 145 | 18 | 0 |
| | 20 | 162 | 17 | 0 |

The compounds of this invention are all very soluble in water and insoluble in organic solvents such as isopropanol, acetone, hexane, trichloroethane, toluene, and the like. They are, furthermore, non-foaming, which is an important property because it makes these compounds suitable for use as anti-microbial agents in products and processes where the generation of foam would be undesirable.

In the formulations shown in Example 28 to 32, the product of Example 4, for economy of space, is written as "Polymer B".

EXAMPLE 28

| Hair Shampoos | | | | |
|---|---|---|---|---|
| Components | Percent by weight | | | |
| "Polymer B" | 5 | 5 | 5 | 5 |
| "Miranol C 2M-SF" | 32 | — | — | — |
| "Maprofix 60S" | 10 | — | — | — |
| "Superamide GR" | 2 | 5 | — | — |
| "Maprofix RH" | — | 43 | — | 50 |
| "Maprofix 60N" | — | — | 25 | — |
| lauryl dimethyl betaine | — | — | 25 | — |
| "Sandopan TFL" | — | — | 4.2 | — |
| propylene glycol | 2 | 1 | 5 | — |
| deionized water | 48 | 45.6 | 35.7 | 44.5 |
| colorants, perfumes and other additives | 1 | 0.4 | 0.1 | 0.5 |

-continued

| Hair Shampoos | | | | |
|---|---|---|---|---|
| Components | Percent by weight | | | |
| pH | 5.5 | 6.8 | 5.8 | 6.1 |

EXAMPLE 29

| Clear Combing Aid and Hair Rinse | | | | |
|---|---|---|---|---|
| "Polymer B" | 2.5 | 6.95 | 6.95 | 6.9 |
| "Tergitol 15-S-12" | 0.1 | — | — | — |
| "Onyxide 500" | 0.1 | — | — | — |
| "Natrosol 250-HH" (3% aqueous solution) | — | 93 | — | — |
| "Klucel HF" (3% aqueous solution) | — | — | 93 | — |
| "Klucel LF" (3% aqueous solution) | — | — | — | 93 |
| propylene glycol | 10 | — | — | — |
| deionized water | 87.25 | — | — | — |
| colorant, perfumes and other additives | 0.05 | 0.05 | 0.05 | 0.1 |
| pH | 5.4 | 5.2 | — | 5.4 |

EXAMPLE 30

| Opaque Hair Rinse | |
|---|---|
| "Polymer B" | 5 |
| "Ammonyx 4" | 5 |
| "Onyxide 500" | 0.05 |
| "Peg 6000 Distearate" | 2.0 |
| "Onyxol 42" | 2.0 |
| cetyl alcohol | 0.5 |
| deionized water | 84.35 |
| colorants, perfumes and other additives | 1.1 |
| pH | 5.5 |

EXAMPLE 31

| Pearlscent Hair Rinse and Hair Set | |
|---|---|
| "Polymer B" | 5 |
| "Peg 6000 Distearate" | 2.5 |
| "Onyxide 500" | 9.1 |
| deionized water | 92.35 |
| colorants, perfumes and other additives | 0.05 |
| pH | 5.7 |

EXAMPLE 32

| Clear Hair Setting Lotion | |
|---|---|
| "Polymer B" | 7.5 |
| deionized water | 92.49 |
| colorants, perfumes and other additives | 0.01 |
| pH | 5.5 |

The proprietary components used in the above formulations and their sources are as follows:

"Miranol C-2M-SF" is an amphoteric surfactant, manufactured by Miranol Chemical Co., Irvington, New Jersey.

"Ammonyx 4", stearyl dimethyl benzyl ammonium chloride; "Maprofix 60S", sodium lauryl ether sulfate; "Maprofix RH", sodium lauryl ether sulfate/amphoteric blend; "Superamide 6R", coco diethanolamide; "Onyxide 500", 2-bromo-2-nitro-1,3-propanediol; and "Onyxol 42", stearyl diethanolamide; are all manufactured by the Onyx Chemical Company, Jersey City, New Jersey.

"Sandopan TFL", is a surfactant manufactured by the Sandoz Chemical Company, East Hanover, New Jersey.

"Natrosol 250-HH", hydroxyethyl cellulose; "Klucel HF", hydroxy propyl cellulose; and "Klucel LF", hydroxypropyl cellulose; are all manufactured by the Hercules Chemical Company, New York, New York.

"Peg 6000 Di-Stearate" is the di-stearate of polyethylene glycol having a molecular weight of 6000.

"Drakeol #7" is a mineral oil having a viscosity of 65/73 Saybolt, manufactured by Drake Refining Company, Butler, Pennsylvania.

The formulations disclosed in Examples 28 to 32 were formulated for the purpose of showing how the products of the present invention may be used for the preparation of hair conditioning toiletries, but are not intended to be limitative with regard to the substitution of equivalent components or concentrations.

Formulations containing "Polymer B" in concentrations of less than one-half of one percent, with or without the usual additives found in hair conditioning preparations, exhibited none of the usual desirable properties expected of a hair conditioner. Tresses to which such preparations were applied exhibited extreme "drag" in wet combing and left a course feeling to the tresses after dry combing. However, formulations in which the concentrations of "Polymer B" was above one-half of one percent, but less than one percent, did impart a smooth conditioned feeling to the tresses after dry combing, although there was no reduction in "drag" upon wet combing.

Formulations in which "Polymer B" is present in a concentration of one percent and greater, and particularly where the concentration is between about 1 to about 10 percent, have all the desirable characteristics mentioned previously, while, as indicated above, at a concentration of 10% or above, the product is at least an effective emulsifier for water-in-oil emulsions. Therefore, the present product may be included in hair creams even without the presence of other emulsifiers.

The aqueous-system hair conditioning products having the formulae of Examples 28 to 32 were all prepared by substantially the same procedure. Such procedure is generally well-known in the art and is not intended to be limitative since modification for specific purposes may be made within the skill of the art. The procedure was as follows:

The water was heated to about 70° C; then while maintaining constant agitation (stirring), the water-soluble materials (i.e. surfactants, humectants, thickeners, etc. and, finally "Polymer B") were added slowly. Then the water-insoluble materials were added slowly, while still under agitation; after which the mixture was permitted to cool to about 40° C. Perfumes and colorants were then added and the pH was adjusted with 20% citric acid agitation being maintained throughout this period. Agitation was maintained until the mixture reached room temperature and was uniform.

The water-insoluble materials in Examples 5 and 6 are the fatty acid ester "Peg 6000 Distearate" and the cetyl alcohol.

The invention claimed is:

1. A polymeric quaternary ammonium compound and mixtures thereof of formula:

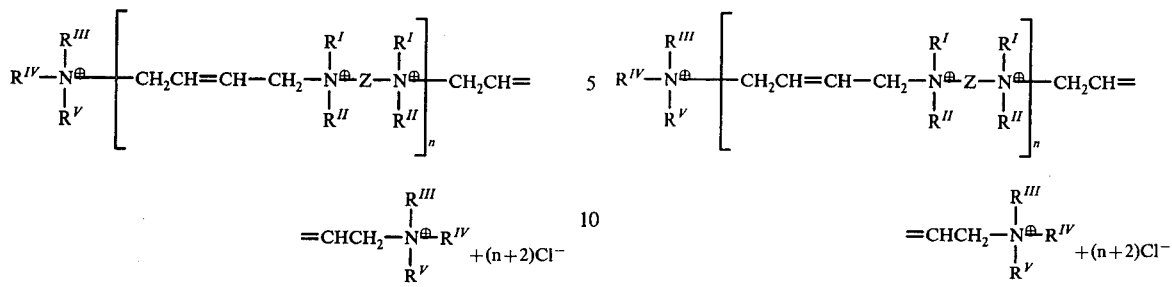

wherein Z represents either (1) a divalent aliphatic radical of from 2 to 10 carbon atoms containing from 0 to 2 hydroxyl substituents and from 0 to 2 ethylenic double bonds, and $R^I$ and $R^{II}$ may either be (A) the same or different and may be either (a) an alkyl group of from 1 to 20 carbon atoms having from 0 to 2 hydroxyl substituents, (b) benzyl, (c) benzyl in which the benzene moiety has one alkyl substituent of from 2 to 20 carbon atoms, or (d) benzyl in which the benzene moiety has from 1 to 5 methyl substituents; (B) $R^I$ and $R^{II}$, taken together with N, form a saturated or unsaturated heterocyclic ring of from 5 to 7 atoms; or (C) $R^I$ and $R^{II}$, taken together with N, and combined with an oxygen atom form a N-moropholino group; or (2) Z represents two divalent ethylene radicals, in which case $R^{II}$ is absent and $R^I$ represents (a) an aliphatic radical of from 1 to 20 carbon atoms having from 0 to 2 hydroxyl substituents, (b) benzyl, (c) benzyl in which the benzene moiety has an alkyl substituent of from 2 to 20 carbon atoms; or (d) benzyl in which the benzene moiety has from 1 to 5 methyl substituents; or (3) Z represents three divalent ethylene radicals in which case $R^I$ and $R^{II}$ are both absent; where (1) $R^{III}$ is an aliphatic radical of from 1 to 20 carbon atoms, having from 0 to 2 hydroxyl substituents, and $R^{IV}$ and $R^V$ may either be (a) the same or different and represent an aliphatic radical having from 1 to 4 carbon atoms with from 0 to 1 hydroxyl substituents (b) taken together with N to form a saturated or unsaturated heterocyclic ring of from 5 to 7 atoms; (c) taken together with N, and combined with an oxygen atom to form a N-morpholino group; or where (2) $R^{III}$, $R^{IV}$, $R^V$ and N, taken together, represent quinoline, isoquinoline or hexamethylene tetramine; and n is a number of from 1 to 15.

2. The mixture of claim 1 wherein at least 50% of the mixture consists of compounds in which n is 2 to 5.

3. The method of conditioning hair which comprises applying to the hair a conditioningly effective amount of an anti-microbial polymeric quaternary ammonium compound or of a mixture of such compounds, said compound having the formula:

wherein Z represents either (1) a divalent aliphatic radical of from 2 to 10 carbon atoms containing from 0 to 2 hydroxyl substituents and from 0 to 2 ethylenic double bonds, and $R^I$ and $R^{II}$ may either be (A) the same or different and may be either (a) an alkyl group of from 1 to 20 carbon atoms having from 0 to 2 hydroxyl substituents, (b) benzyl, (c) benzyl in which the benzene moiety has one alkyl substituent of from 2 to 20 carbon atoms, or (d) benzyl in which the benzene moiety has from 1 to 5 methyl substituents; (B) $R^I$ and $R^{II}$, taken together with N, form a saturated or unsaturated heterocyclic ring of from 5 to 7 atoms; or (C) $R^I$ and $R^{II}$, taken together with N, and combined with an oxygen atom, form a N-moropholino group; or (2) Z represents two divalent ethylene radicals, in which case $R^{II}$ is absent and $R^I$ represents (a) an aliphatic radical of from 1 to 20 carbon atoms having from 0 to 2 hydroxyl substituents, (b) benzyl, (c) benzyl in which the benzene moiety has an alkyl substituent of from 2 to 20 carbon atoms; or (d) benzyl in which the benzene moiety has from 1 to 5 methyl substituents; or (3) Z represents three divalent ethylene radicals in which case $R^I$ and $R^{II}$ are both absent; where (1) $R^{III}$ is an aliphatic radical of from 1 to 20 carbon atoms, having from 0 to 2 hydroxyl substituents, and $R^{IV}$ and $R^V$ may either be (a) the same or different and represent an aliphatic radical having from 1 to 4 carbon atoms with from 0 to 1 hydroxyl substituents (b) taken together with N to form a saturated or unsaturated heterocyclic ring of from 5 to 7 atoms; (c) taken together with N, and combined with an oxygen atom, to form a N-morpholino group; or where (2) $R^{III}$, $R^{IV}$, $R^V$ and N, taken together, represent quinoline, isoquinoline or hexamethylene tetramine; and n is a number of from 1 to 15.

4. The method of claim 3 wherein a mixture of said compounds is used and wherein at least 50% of the mixture consists of compounds in which n is 2 to 5.

5. The compound of claim 1 wherein $R^I=R^{II}=$ —$CH_3$, $R^{III}=R^{IV}=R^V=$ —$CH_2$—$CH_2OH$, and Z is —$CH_2CH=CH$—$CH_2$—.

6. The method of claim 3 wherein $R^I=R^{II}=$—$CH_3$, $R^{III}=R^{IV}=R^V=$ —$CH_2$—$CH_2OH$, and Z is —$CH_2CH=CH$—$CH_2$—.

* * * * *